(12) United States Patent
Lutz et al.

(10) Patent No.: US 6,463,322 B1
(45) Date of Patent: Oct. 8, 2002

(54) COMBINATION REFERENTIAL AND DIFFERENTIAL AMPLIFIER FOR MEDICAL SIGNAL MONITORING

(75) Inventors: William J. Lutz, Middleton; Daniel J. Lombardi, Verona, both of WI (US)

(73) Assignee: Viasys Healthcare, Inc., Madison, WI (US)

( * ) Notice: Subject to any disclaimer, the term of this patent is extended or adjusted under 35 U.S.C. 154(b) by 0 days.

(21) Appl. No.: 09/832,247

(22) Filed: Apr. 10, 2001

(51) Int. Cl.⁷ .................................................. A61B 5/04
(52) U.S. Cl. ........................................ 600/546; 600/544
(58) Field of Search ................................. 600/544, 545, 600/300, 372, 378, 374, 382, 383, 546, 547

(56) References Cited

U.S. PATENT DOCUMENTS

| | | | |
|---|---|---|---|
| 3,628,527 A | * 12/1971 | West | ........................ 330/1 R |
| 4,530,365 A | 7/1985 | Harada et al. | |
| 4,846,190 A | 7/1989 | John | |
| 5,269,315 A | 12/1993 | Leuchter et al. | |
| 5,275,172 A | 1/1994 | Ives | |
| 5,309,923 A | 5/1994 | Leuchter et al. | |
| 5,368,041 A | 11/1994 | Shambroom | |
| 5,381,804 A | 1/1995 | Shambroom | |
| 5,450,855 A | 9/1995 | Rosenfeld | |
| 5,501,230 A | * 3/1996 | Laribiere | .................... 600/508 |
| 5,540,235 A | 7/1996 | Wilson | |
| 5,755,230 A | * 5/1998 | Schmidt et al. | ............. 600/376 |
| 5,813,404 A | 9/1998 | Devlin et al. | |
| 6,259,938 B1 | * 7/2001 | Zarychta et al. | ............ 600/380 |

OTHER PUBLICATIONS

Nicolet Instrument Corporation, Spirit Service Manual, pp. 2–15–2–18, 1991, Madison Wisconsin.
Wim Van Drongelen, U.S. patent application No. 09/295,167, entitled Medical Signal Monitoring and Display, filed Apr. 20, 1999.
William J. Lutz, U.S. patent application No. 09/320,613, entitled Time Frame Synchronization of Medical Monitoring Signals, filed May 26, 1999.
Nicolet Biomedical, Spirit 2000 and Spirit 2000 Lite Evoked Potential Reference Guide, p. 12–7, Jan. 2000, Madison, Wisconsin.

* cited by examiner

Primary Examiner—Kevin Shaver
Assistant Examiner—Navin Natnithithadha
(74) Attorney, Agent, or Firm—Foley & Lardner

(57) ABSTRACT

A combination referential and differential amplifier circuit for a medical signal monitoring system includes a plurality of electrode inputs, including at least one reference electrode input, a plurality of medical signal amplifiers, and switching means for selectively coupling each of the plurality of electrode inputs to each of the inputs of the plurality of medical signal amplifiers. Each electrode input may be selectively coupled to several amplifier inputs. The output of a medical signal amplifier with the amplifier inputs thereof coupled to electrode inputs, neither of which is a reference electrode input, produces a differential amplifier signal output. A medical signal amplifier with the inputs thereof coupled to electrode inputs, one of which is the reference electrode input, produces a referential signal output. Thus, a combination of differential and referential electrophysiologic signal channels may be provided.

10 Claims, 3 Drawing Sheets

FIG. 3

Amplifier Settings

Channel
- Input: One
+ Input: REF
Label: 01

Low Frequency: 0.2 Hz
High Frequency: 500 Hz
Amplifier Gain: 500

Slope Low Frequency: ● 6  ○ 12

☐ Sound
☑ Disconnect Selection

01  Update

Referential Mode

Amplifier
COM: ● 1  ○ 2  ○ 3  ○ 4
REF: ● 1  ○ 2  ○ 3  ○ 4

☐ Disconnect Channels

OK
Cancel

Input Labels

| Chan. | Mode | - Input | + Input | Label | Amplifier Gain | Low Freq. | High Freq. | Slope Low | Notch |
|---|---|---|---|---|---|---|---|---|---|
| 1 | Refer... | 01 | REF | 01 | 500 | 0.2 | 500 | 12 | On |
| 2 | Refer... | 02 | REF | 02 | 500 | 0.2 | 500 | 12 | On |
| 3 | Refer... | 03 | REF | 03 | 500 | 0.2 | 500 | 12 | On |
| 4 | Refer... | 04 | REF | 04 | 500 | 0.2 | 500 | 12 | On |
| 5 | Differe... | 10 | 11 | 10-11 | 500 | 0.2 | 5000 | 12 | On |
| 6 | Differe... | 12 | 13 | 12-13 | 500 | 0.2 | 5000 | 12 | On |
| 7 | Differe... | 14 | 16 | 14-15 | 500 | 0.2 | 5000 | 12 | On |
| 8 | Differe... | 16 | 17 | 16-17 | 500 | 0.2 | 5000 | 12 | On |

COMBINATION REFERENTIAL AND DIFFERENTIAL AMPLIFIER FOR MEDICAL SIGNAL MONITORING

FIELD OF THE INVENTION

The present invention pertains generally to medical monitoring methods and devices for analyzing and displaying electrophysiologic signals, and more particularly to systems and methods for amplifying electrophysiologic signals detected at electrodes placed on a subject to provide amplified electrophysiologic signals to such a medical monitoring device.

BACKGROUND OF THE INVENTION

Medical monitoring involves monitoring the body of a subject to determine the state of health of the subject and to detect, identify, and diagnose changes or abnormalities in the state of the body which may be indicative of problems, or for treatment evaluation. Medical monitoring may involve, for example, monitoring the motion of a subject's body, temperature or chemical changes of the subject's body, and/or audible or electrical signals reflected or generated by the subject's body. For example, electroencephalography (EEG) is a form of medical monitoring wherein the electrical potentials of the subject's brain are monitored by attaching electrodes to the subject's scalp. In electromyography (EMG), electrical activity generated in the subject's muscles is monitored using surface and/or needle recording electrodes. Medical monitoring may take place when a subject is at rest, in motion, or during the performance of a medical procedure. In some cases, medical monitoring involves monitoring the response of a subject to a stimulus. For example, evoked potential (EP) monitoring may be used to detect the electrical response of a subject's nervous system to audible, visual, or electrical stimuli. Medical monitoring involving stimulus and response detection may be used in combination with EMG and various other medical monitoring methods as well.

Monitoring of the various physiologic signals generated by a subject's body is typically performed using dedicated devices and/or systems. For example, EEG monitoring may be performed using a dedicated EEG monitoring system, by attaching electrodes to a subject to detect the electrical potential of the subject's brain, amplifying and filtering the signals received from the electrodes for the desired frequency range of interest for EEG analysis, and providing the amplified and filtered signals to an EEG analysis system including software for further manipulating the EEG signals for analysis and a display on an EEG system monitor. Similarly, EMG monitoring may be performed using a dedicated EMG monitoring system, by placing electrodes on the subject to detect electrical activity generated in the subject's muscles, amplifying and filtering the signals detected by the electrodes for the desired frequency range of interest for EMG signals, and providing the amplified and filtered signals to an EMG analysis system including software for further manipulating the EMG signals for analysis and display on an EMG system monitor. Other signals of interest, e.g., vital signs, may be monitored in a similar manner, with a separate dedicated system provided for each type or modality of monitored signal of interest. Each such dedicated monitoring system may include or be connected to a system for providing stimulus to a subject, and for analyzing the particular detected signal of interest in response to the stimulus provided.

U.S. patent application Ser. No. 09/295,167, entitled "Medical Signal Monitoring and Display," by Wim van Drongelen, and assigned to the assignee of the present application, describes a medical signal monitoring system and method providing the capability for an operator of the system to display and analyze physiologic signals of various types, frequencies, and modalities. Such a system may be provided with data from various physiologic signal acquisition systems, including systems for acquiring electrophysiologic signals from electrodes positioned on a subject. The system may further be connected to auditory, visual, and/or electrical stimulator systems, for controlling the providing of stimulation to a subject, while analyzing the physiologic signals received in response to the stimulus provided. Such a system includes an operator-friendly user interface which allows an operator of the system to designate and control, display, and analyze the physiologic signals received by the system and stimulus provided thereby. Such an integrated system provides a full range of diagnostic capability in a single device for use in a doctor's office, operating room, intensive care unit, or emergency department.

In a typical application of a medical signal monitoring system, a plurality of electrodes may be attached to the body of a subject. Electrophysiologic signals, picked up by the electrodes, are carried by leads to a signal amplifier which may be part of or separate from the medical monitoring system. The amplified signals may, for example, be filtered, digitized, and provided to the medical monitoring system for analysis and display. In this manner, several electrophysiologic signals, e.g., EEG and EMG signals, produced by a subject may be monitored continuously or periodically.

Electrophysiologic signals to be displayed and analyzed by a medical signal monitoring system are typically derived from the signals picked up by electrodes placed on a subject's body in one of two ways, as either differential or referential electrophysiologic signals. Differential electrophysiologic signals are derived from the difference between the signals detected at two electrodes placed in a desired position on the subject. Differential electrophysiologic signals are typically derived by connecting the signals provided from each of two electrodes positioned on a subject to each of the two inputs of a differential amplifier. The output of the differential amplifier is an analog differential physiologic signal, which may be filtered for a desired frequency range of interest and converted, by an analog-to-digital converter, to a digital differential physiologic signal which is provided to a medical signal monitoring system for analysis and display. Referential electrophysiologic signals are derived from the signal detected at an electrode placed in a desired position on the subject with reference to a reference electrode placed on the subject. Multiple referential physiologic signals may be determined in this way by employing multiple electrodes positioned on the subject and by detecting the signals detected at each of these multiple electrodes with reference to a single reference electrode. Amplified referential physiologic signals may be filtered and digitized for analysis and display on a medical signal monitoring system. Selected differential physiologic signals may be obtained by combining multiple referential physiologic signals which are obtained using the same reference signal. This may be achieved by subtracting one digitized referential signal from another digitized referential signal to obtain the desired differential signal.

Typical medical signal monitoring systems are designed to employ electrodes positioned on the subject for either differential or referential signal detection, and include the appropriate amplifier and analysis circuitry and software for the type of signal (differential or referential) to be processed. For example, the Spirit signal monitoring system, made by Nicolet Instrument Corp., allowed a user to define up to four differential channels of, e.g., EEG signals. Cross-point switching devices were employed in the system to connect selected electrode input signals to the inputs of selected differential amplifier circuits to define differential signal channels of interest. Any combination of electrode inputs could be coupled by the switches to the amplifier channels. Some more advanced medical signal monitoring systems provide both differential and referential electrophysiologic signal detection. Such a system may allow an operator to select whether the input signals provided from electrodes to the system are to be interpreted as differential or a referential signal inputs. The medical signal monitoring system then amplifies and analyzes the signals received in such channels in an appropriate manner for the type of channel (differential or referential) selected.

What is desired is a medical signal monitoring system which receives and analyzes electrophysiologic signals from a plurality of electrodes positioned on a subject, which allows an operator of the system to select whether the signal received from each electrode is to be amplified in a differential or referential mode, and in which a signal received from any given electrode may be amplified in a combination of differential and referential signal channels. Thus, what is desired is a medical signal monitoring system which provides a user selectable combination of amplified differential and referential electrophysiologic signals from a set of electrode input signals.

SUMMARY OF THE INVENTION

The present invention provides a medical signal monitoring system and method which provides a selectable combination of referential and differential medical signals for analysis and display. A system and method in accordance with the present invention employs a combination referential and differential amplifier circuit. A combination referential and differential amplifier circuit in accordance with the present invention includes a plurality of electrode inputs, a plurality of medical signal amplifiers, and a switching device for selectively coupling each of the plurality of electrode inputs to the plurality of medical signal amplifiers in a manner so as to provide simultaneously a combination of referential and differential electrophysiologic signals for analysis and display on a medical signal monitoring system.

A combination referential and differential amplifier circuit in accordance with the present invention includes a plurality of electrode inputs. Each of the electrode inputs is adapted to be coupled to an electrode positioned on a subject for detecting electrophysiologic signals of the subject. At least one of the plurality of electrode inputs to the combination referential and differential amplifier circuit is a reference electrode input. The reference electrode input to the combination referential and differential amplifier circuit may be buffered in a conventional manner, to prevent unbalance between the referential signal, which will employ the electrophysiologic signal input to the reference electrode input of the combination referential and differential amplifier circuit, and other electrode input signals, which will be paired with the reference input signal. Thus, a single buffered reference electrode input signal may be used in combination with many other electrode input signals to define multiple referential signal channels.

A combination referential and differential amplifier circuit in accordance with the present invention also includes a plurality of medical signal amplifiers. Each of the plurality of medical signal amplifiers may be implemented in a conventional manner as a differential amplifier circuit including two amplifier inputs. The output of each of the plurality of medical signal amplifiers is the amplified difference between the signals provided at the inputs to each of the medical signal amplifiers. The medical signal amplifiers employed in the combination referential and differential amplifier circuit are preferably selected to operate in the frequency range of the type of electrophysiologic signals to be amplified, e.g., EEG, EMG, EP signals, etc., and to provide sufficient amplification for the given signal level of the signals of interest.

A switching device is provided between the plurality of electrode inputs and the plurality of medical signal amplifiers in a combination referential and differential amplifier circuit in accordance with the present invention. The switching device is employed for selectively coupling each of the plurality of electrode inputs of the combination referential and differential amplifier circuit to the amplifier inputs of the plurality of medical signal amplifiers. The amplifier output of medical signal amplifiers with the amplifier inputs thereof coupled via the switching device to different electrode inputs, neither of which is the reference electrode input, produces a differential amplifier signal output. The amplifier output of medical signal amplifiers with the amplifier inputs thereof coupled via the switching device to different electrode inputs, one of which is the reference electrode input, produces a referential signal output. Thus, a combination referential and differential amplifier circuit in accordance with the present invention may be employed to provide a combination of user-defined differential and referential electrophysiologic signals for display and analysis by a medical signal monitoring system.

In accordance with the present invention, the switching device preferably enables a single electrode input to be coupled simultaneously to the input of any of the plurality of medical signal amplifiers, in combination with any other electrode input, including the reference electrode input. Thus, in accordance with the present invention, a single electrophysiologic electrode input signal may be employed to generate a variety of different differential and referential electrophysiologic signals for analysis and display.

In accordance with the present invention, the switching device may preferably be implemented as a solid state integrated circuit cross-point switching device, which may be controlled by an operator to provide the desired switching device functionality. The switching device may preferably be controlled by control signals provided from the system processor of an integrated medical signal monitoring system with which a combination referential and differential amplifier circuit in accordance with the present invention is employed. The system processor may preferably generate a graphical user interface, which may be used by an operator to select which electrode inputs of the combination referential and differential amplifier circuit are to be coupled to which medical signal amplifiers of the amplifier circuit. Thus, the graphical user interface may be used by an operator to define various referential and differential electrophysiologic signal channels from the available electrode inputs. The medical signal monitoring system processor preferably controls the switching device of the combination referential and differential amplifier circuit to implement automatically the desired combination of differential and referential signal channels in response to the operator selections.

Further objects, features, and advantages of the invention will be apparent from the following detailed description taken in conjunction with the accompanying drawings.

BRIEF DESCRIPTION OF THE DRAWINGS

In the drawings:

FIG. 3 is a screen display showing an exemplary graphical user interface generated by a medical signal monitoring system processor whereby an operator of the system may define a combination of differential and referential signal channels from a plurality of available electrode inputs, and wherein the medical signal monitoring system processor controls a combination referential and differential amplifier circuit in accordance with the present invention to implement automatically the selections made by the operator using the graphical user interface.

DETAILED DESCRIPTION OF THE PREFERRED EMBODIMENTS

Figure 1:
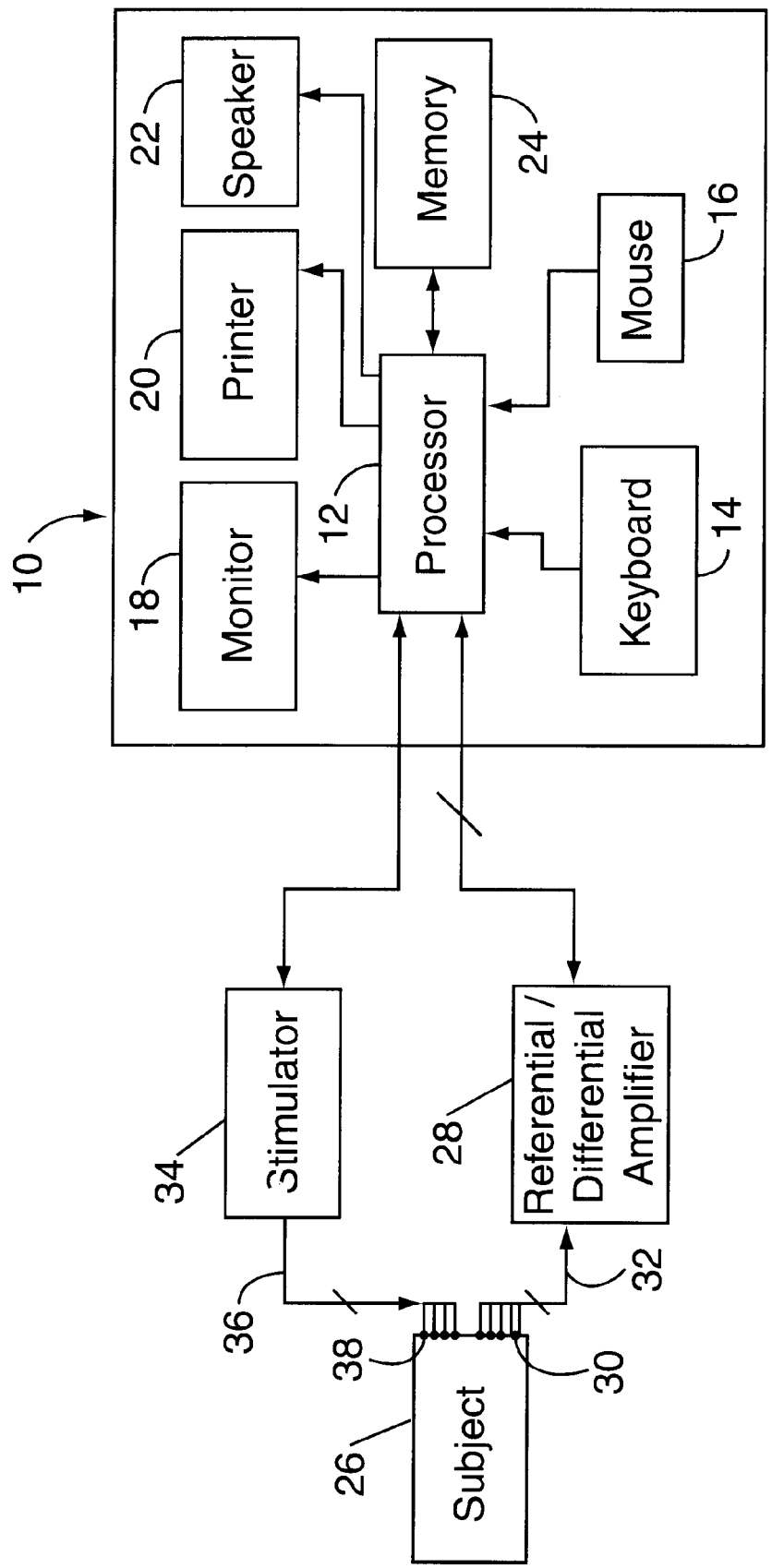
FIG. 1 is a schematic block diagram of an exemplary medical signal monitoring system employing a combination referential and differential amplifier circuit in accordance with the present invention.

The present invention provides a system and method for providing a user selectable combination of amplified differential and referential electrophysiologic signals for analysis and display by a medical signal monitoring system. The present invention will be described herein with reference to the exemplary incorporation thereof into an integrated medical signal monitoring system which may be used for monitoring and analyzing a variety of electrophysiologic signals, as well as for providing electrical and other stimulus to a subject and detecting and analyzing the subject's response thereto. Such an integrated medical signal monitoring system is described, for example, in U.S. patent application Ser. No. 09/295,167, entitled "Medical Signal Monitoring and Display," filed on Apr. 20, 1999, by Wim van Drongelen, and assigned to the assignee of the present application, the disclosure of which is incorporated herein by reference. It should be understood, however, that the present invention may also be incorporated in, and used in combination with, other and/or more basic medical signal monitoring systems which are only designed to monitor a single type or modality of electrophysiologic signal.

A basic hardware configuration for an exemplary medical signal monitoring system 10 incorporating and employing a combination referential and differential amplifier circuit in accordance with the present invention is illustrated in, and will be described in detail with reference to, FIG. 1. The medical signal monitoring system 10 may be implemented using a conventional computer system having conventional computer peripheral devices. For example, the monitoring system 10 may be implemented on a conventional personal computer processor 12. Due to the large number of computations performed by the processor 12, a computer employing a fast processor, such as a Pentium 800 MHz processor, or faster, is preferred. It should be understood that the present invention may be implemented using other types of general purpose or special purpose programmable computers or processors 12.

The processor 12 is preferably provided with conventional computer peripherals. For example, the processor 12 preferably includes conventional input devices such as, for example, a keyboard 14 and mouse 16. Other types of input devices, such as a microphone for voice recognition control of the system, may be employed. Conventional output devices which may be employed with the processor 12 include a computer monitor 18, printer 20, and speaker 22 for providing audio output from the processor 12. The processor 12 preferably is also provided with conventional computer memory 24, including a large disk storage capability.

The monitoring system 10 receives physiologic signals from a subject 26 via a combination referential and differential amplifier circuit 28 in accordance with the present invention. The combination referential and differential amplifier circuit 28 will be described in more detail below. It should be noted that the amplifier circuit 28 may be separate from or included as part of the medical signal monitoring system 10. The amplifier circuit 28 may be connected to the subject 26 by, for example, electrodes 30 placed on the subject 26. The electrodes 30, which may be conventional electrodes as are well known in the art, pick up electrophysiologic signals of the subject 26 and provide the signals, via the leads 32, to the amplifier circuit 28. The amplifier circuit 28 amplifies the signals received from the electrodes 30, may provide some preliminary filtering of the signals, and then provides the amplified and preliminarily filtered signals to the monitoring system 10 for analysis and display. In a dedicated EEG, EP, or EMG system, the amplifier circuit 28 may filter the electrode signals to a relatively narrow band of interest. However, for an integrated system, as described in the above-referenced U.S. patent application Ser. No. 09/295,167, wherein electrophysiologic signals across a broad frequency range are displayed and analyzed, a broad band of frequencies should be passed by the amplifier circuit 28 to the monitoring system 10 (e.g., at least broad enough to include the EEG and EMG bands). The signals provided to the monitoring system 10 from the amplifier circuit 28 are, therefore, preferably essentially broad band signals. The signals provided by the amplifier circuit 28 to the system 10 are preferably converted to digital signals, using conventional analog-to-digital converter technology, before being provided to the system 10. This reduces susceptibility to noise artifacts on the cable connecting the amplifier circuit 28 to the medical signal monitoring system 10.

The medical signal monitoring system 10 may also control the providing of stimulation signals to the subject 26 via one or more stimulator systems 34. Various different types of stimulator systems 34 may be employed, including stimulator systems for providing electrical, auditory, and/or visual stimulation. The stimulator systems 34 may be connected to the subject 26 via, for example, conventional leads 36 and electrodes 38 positioned on the subject 26 for providing electrical stimulation to the subject 26. The stimulator system 34 preferably provides a signal back to the monitoring system 10 indicating the time at which a stimulation signal is provided to the subject 26. This signal allows the monitoring system 10 to synchronize the stimulation signals provided to the subject 26 with response signals received from the amplifier circuit 28 for proper analysis and display of the relationship between the stimulus and response signals.

It should be understood that each of the hardware components illustrated in FIG. 1 may be implemented in a conventional manner, using conventional commercially available hardware. Also, the various hardware systems illustrated in FIG. 1 may be connected together in a conventional manner, using conventional leads, cabling, connectors, etc. Alternatively, the various hardware systems illustrated in FIG. 1 may be connected together via a network bus topology, such as, for example, an IEEE 1394 high-speed serial bus topology. In the latter case, the stimulus signals provided by the stimulator device 34 and the response signals detected by the amplifier circuit 28 may be time frame synchronized in the manner described in co-pending U.S. patent application Ser. No. 09/320,613, entitled "Time Frame Synchronization of Medical Monitoring Signals," filed on May 26, 1999, by William J. Lutz, and assigned to the assignee of the present application.

Figure 2:
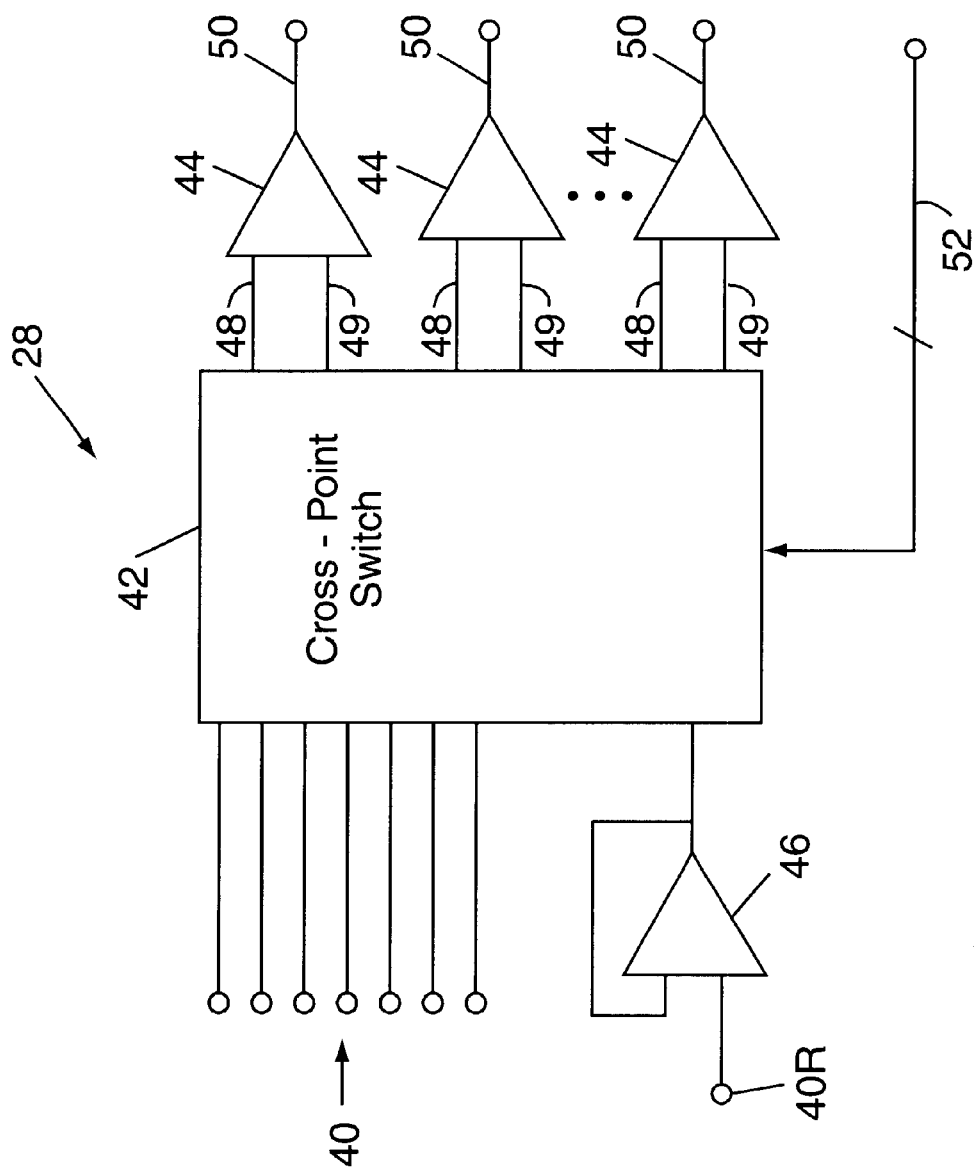
FIG. 2 is a schematic block diagram of an exemplary combination referential and differential amplifier circuit in accordance with the present invention.

An exemplary combination referential and differential amplifier circuit 28 in accordance with the present invention will now be described in detail with reference to FIG. 2. Note that conventional filter and analogto-digital converter circuitry may be included as part of the combination referential and differential amplifier circuit 28, as described above. For clarity, such conventional circuitry is not illustrated in FIG. 2, and will not be described in further detail herein.

A combination referential and differential amplifier circuit 28 in accordance with the present invention includes a plurality of electrode inputs 40, a switching device 42, and a plurality of medical signal amplifiers 44.

The plurality of electrode inputs 40 are adapted to be coupled to electrodes 30 for detecting the electrophysiologic signals of a subject 26. At least one of the plurality of electrode inputs 40 is a reference electrode input 40R. Of course, more than one of the plurality of electrode inputs 40 may be a reference electrode input. For example, multiple reference electrode inputs may be provided for obtaining referential signals with different reference inputs from different parts of a subject's body. A conventional pre-amplifier/buffer circuit 46 is preferably coupled between the reference input 40R and the switching device 42. The buffer circuit 46 should be designed for the signals to be detected by the medical signal monitoring system 10 with which the combination referential and differential amplifier circuit 28 is employed to prevent unbalance between amplified referential electrophysiologic signals produced by the amplifier circuit 28, which employ the reference electrode input 40R, and other electrode input signals which will be paired with the reference electrode input 40R. Buffering of the reference electrode input 40R assures that the common mode will not be adversely affected when the reference input 40R is coupled to several amplifiers along with other electrode inputs 40, as will be discussed in more detail below, to define multiple referential signal channels using the same reference signal. Other ones of the plurality of electrode inputs 40 may also be pre-amplified/buffered, as necessary or desired.

The plurality of medical signal amplifiers 44 may preferably be implemented in a conventional manner using conventional discreet or integrated solid state differential amplifier circuits 44. Appropriate medical signal amplifiers 44 are preferably selected for the desired signal strength and frequency range of the electrophysiologic signals to be amplified by the combination referential and differential amplifier circuit 28. Each of the plurality of medical signal amplifiers has two amplifier inputs 48 and 49, and an amplifier output 50. The signal provided on the amplifier output 50 of each medical signal amplifier 44 is the amplified difference of the signals provided at the medical signal amplifier inputs 48 and 49. The analog signals provided on the medical signal amplifier outputs 50 may be filtered and/or converted to digital signals in a conventional manner, before being provided to the medical signal monitoring system 10 for analysis and display.

The switching device 42 is coupled between the plurality of electrode inputs 40 and the amplifier inputs 48 and 49 of the medical signal amplifiers 44. The switching device 42 provides a means for coupling selectively each of the plurality of electrode inputs 40 to each of the amplifier inputs 48 and 49 of the plurality of medical signal amplifiers 44. The amplifier output 50 of a medical signal amplifier 44 with the amplifier inputs 48 and 49 thereof coupled to different electrode inputs 40, neither of which is a reference electrode input 40R, provides a differential electrophysiologic signal output. The amplifier output 50 of a medical signal amplifier 44 with the amplifier inputs 48 and 49 thereof coupled to different electrode inputs 40, one of which is the reference electrode input 40R, provides a referential electrophysiologic signal output. Thus, by controlling the switching device 42 in an appropriate manner, a combination referential and differential amplifier circuit 28 in accordance with the present invention may be used to provide a combination of differential and referential electrophysiologic signals for analysis and display by a medical signal monitoring system 10. Differential and referential electrophysiologic signals provided by the combination referential and differential amplifier circuit 28 may be processed for display and analysis by the medical signal monitoring system 10 in a conventional manner. Various differential electrophysiologic signals may be derived from referential electrophysiologic signals provided by the combination referential and differential amplifier circuit 28 by montaging referential signals employing the same reference input together in a known manner.

Preferably, the switching device 42 allows any one of the electrode inputs 40, 40R to be coupled simultaneously to any amplifier input 48, 49 of any of the medical signal amplifiers 44 coupled to the switching device 42. Thus, a single electrode input signal provided on a single electrode input 40 to the combination referential and differential amplifier circuit 28 may be employed in one or more differential and/or referential signal channels. However, caution should be exercised when coupling non-buffered electrode inputs 40 to more than a few signal channels. Capacitance coupled into the circuit by the switching device 42 can adversely affect the common mode for non-buffered inputs 40 coupled to many amplifiers 44. Buffered reference inputs 40R may be used in a large number of referential signal channels without adverse effects.

The switching device 42 may be implemented using a conventional solid state integrated circuit cross-point switching device. A cross-point switching device includes a plurality of solid state switches which may be operated by command signals, e.g., provided on a command signal line 52 from the medical signal monitoring system processor 12, to couple any one of the plurality of electrode input lines 40 to any one of the amplifier inputs 48 and 49 of the plurality of medical signal amplifiers 44. The size of the cross-point switching device 42 required to implement a combination referential and differential amplifier circuit 28 in accordance with the present invention will depend upon the number of electrode inputs 40 and medical signal amplifiers 44 desired. For example, a combination referential and differential amplifier circuit providing eight electrode inputs 40, including at least one reference electrode input 40R, and eight output signal channels (eight medical signal amplifiers 44) would include 128 switching devices for selectively coupling any one of the electrode inputs 40, 40R to any one of the amplifier inputs 48 and 49 of the plurality of medical signal amplifiers 44, to provide a combination of referential and differential electrophysiologic signal channels. A preferred combination referential and differential amplifier circuit providing 44 electrode inputs, including 4 buffered reference electrode inputs, and 16 output signal channels, would preferably employ 1408 switches, which may be implemented using several integrated circuit cross-point switching device circuit chips.

A medical signal monitoring system 10, including a combination referential and differential amplifier circuit 28 in accordance with the present invention, preferably provides an easy-to-use graphical user interface which allows an operator to identify which of the combination referential and differential amplifier circuit electrode inputs 40, 40R are to be coupled to which of the amplifier inputs 48 and 49 of the plurality of medical signal amplifiers 44 via the switching device 42. In other words, such a graphical user interface preferably allows an operator to define easily a plurality of differential and referential electrophysiologic signal channels from a plurality of available electrode inputs.

An exemplary graphical user interface 60 which may be provided by and employed in a medical signal monitoring system, such as the integrated medical signal monitoring system described in the above-referenced U.S. patent application Ser. No. 09/295,167, to allow a user of such a system to define the signals which are to be detected in each of several differential and referential signal channels, is illustrated in FIG. 3. Such a graphical user interface may be generated in a conventional manner by the system processor 12 of the medical monitoring system 10, and displayed on a system display or monitor 18. An operator may interact with such a user interface 60 in a conventional manner using the system keyboard 14, mouse 16, or another user input device.

The exemplary graphical user interface 60 includes a variety of menu selections 62 for each channel, which allow a user to identify, e.g., the –/+ inputs for each channel, i.e., to identify the signal source (electrode input 40, 40R,) for each amplifier input 48, 49 for the plurality of medical signal amplifiers 44 in the combination referential and differential amplifier circuit 28, and to identify the channel as a referential or differential signal channel. The graphical user interface 50 may also allow the operator to identify a label for each channel, low- and high-frequency cutoff for each channel, amplifier gain, low-frequency cutoff slope, whether audio signals are to be produced from the signal detected on the defined channel, etc. Characteristics of each channel thus defined are displayed in a window 64 provided on the graphical user interface 60. The graphical user interface 60 may be used to define new differential or referential electrophysiologic signal detection channels for an integrated medical signal monitoring system 10 in accordance with the present invention, or to edit previously defined channels. The system processor 12 provides control signals to the switching device 42, e.g., on a line 52, to control the switching device 42 in the manner described above to implement the combination of differential and referential signal channels defined by the operator using the graphical user interface 60. Thus, in accordance with the present invention, the operator of a medical signal monitoring system 10 is provided with an easy and convenient way for deriving a combination of differential and referential electrophysiologic signals for analysis and display on the system 10 from a set of electrode input signals.

It should be understood that the present invention is not limited to the particular exemplary applications and embodiments illustrated and described herein, but embraces all such modified forms thereof as come within the scope of the following claims.

What is claimed is:

1. A medical signal monitoring apparatus including a combination referential and differential amplifier circuit, comprising:

(a) a plurality of electrode inputs adapted to be coupled to electrodes for detecting electrophysiologic signals of a subject, wherein at least one of the plurality of electrode inputs is a reference electrode input;

(b) a plurality of medical signal amplifiers, each of the medical signal amplifiers having a first amplifier input, a second amplifier input, and an amplifier output; and (c) switching means for selectively coupling each of the plurality of electrode inputs to each of the first and second amplifier inputs of the plurality of medical signal amplifiers, such that the amplifier output of a medical signal amplifier with the first and second amplifier inputs thereof coupled to different electrode inputs neither of which is a reference electrode input produces a differential amplifier signal output, and such that the amplifier output of a medical signal amplifier with the first and second amplifier inputs thereof coupled to different electrode inputs one of which is the reference electrode input produces a referential signal output.

2. The medical signal monitoring apparatus of claim 1 wherein the switching means for selectively coupling each of the plurality of electrode inputs to each of the of the first and second amplifier inputs of the plurality of medical signal amplifiers includes a cross point switching device having the plurality of electrode inputs coupled to an input side thereof and the first and second inputs of the plurality of medical signal amplifiers coupled to an output side thereof.

3. The medical signal monitoring apparatus of claim 1 comprising additionally a buffer circuit coupled between the reference electrode input and the switching means.

4. The medical signal monitoring apparatus of claim 1 comprising additionally a system processor for generating a graphical user interface for allowing an operator to select which of the plurality of electrode inputs will be coupled to which of the plurality of medical signal amplifiers thereby to define a combination of differential and referential signal channels and for controlling operation of the switching means in response to the operator selections made using the graphical user interface.

5. The medical signal monitoring system of claim 1 wherein the plurality of electrode inputs are adapted to receive and the plurality of medical signal amplifiers are adapted to amplify electrophysiologic signals selected from the group of electrophysiologic signals consisting of EEG, EMG, and evoked potential signals.

6. A method for controlling a medical signal monitoring apparatus to obtain a selectable combination of referential and differential medical signals, comprising the steps of:

(a) attaching a plurality of electrodes to a subject for detecting electrophysiologic signals of the subject, wherein at least one of the plurality of electrodes attached to the subject is a reference electrode;

(b) providing a plurality of medical signal amplifiers, each of the medical signal amplifiers having a first amplifier input, a second amplifier input, and an amplifier output; and (c) selectively coupling each of the plurality of electrodes to selected ones of the first and second amplifier inputs of the plurality of medical signal amplifiers, such that the amplifier output of a medical signal amplifier with the first and second amplifier inputs thereof coupled to different electrodes neither of which is a reference electrode produces a differential amplifier signal output, and such that the amplifier output of a medical signal amplifier with the first and second amplifier inputs thereof coupled to different electrodes one of which is the reference electrode produces a referential signal output.

7. The method of claim 6 wherein the step of selectively coupling each of the plurality of electrodes to selected ones of the first and second amplifier inputs of the plurality of medical signal amplifiers includes the steps of coupling the plurality of electrodes to the input side of a cross point switching device, coupling the first and second amplifier inputs of each of the plurality of medical signal amplifiers to an output side of the cross point switching device, and controlling the cross point switching device to selectively couple each of the plurality of electrodes to selected ones of the first and second amplifier inputs of the medical signal amplifiers.

8. The method of claim 7 comprising additionally the step of coupling a buffer circuit between the reference electrode and the cross point switching device.

9. The method of claim 6 comprising additionally the steps of generating a graphical user interface for allowing an operator to select which of the plurality of electrode inputs will be coupled to which of the plurality of medical signal amplifiers thereby to define a combination of differential and referential signal channels and selectively coupling each of the plurality of electrodes to selected ones of the first and second amplifier inputs of the plurality of medical signal amplifiers automatically in response to the operator selections made using the graphical user interface.

10. The method of claim 6 wherein the plurality of electrodes are adapted to receive and the plurality of medical signal amplifiers are adapted to amplify electrophysiologic signals selected from the group of electrophysiologic signals consisting of EEG, EMG, and evoked potential signals.

* * * * *